United States Patent

Brown et al.

[11] Patent Number: 4,898,762
[45] Date of Patent: Feb. 6, 1990

[54] EASY TEAR STERILIZATION INDICATOR TAPE

[75] Inventors: Josephine S. Brown; Alan J. Sipinen, both of St. Paul, Minn.

[73] Assignee: Minnesota Mining and Manufacturing Company, St. Paul, Minn.

[21] Appl. No.: 212,661

[22] Filed: Jul. 1, 1988

[51] Int. Cl.$^4$ .............................................. D06N 7/04
[52] U.S. Cl. ..................................... 428/152; 428/155; 428/212; 428/220; 428/343; 428/354; 428/355; 428/500; 428/502; 428/516; 428/906; 428/913; 156/183; 156/184; 156/196; 156/210
[58] Field of Search ............... 428/152, 195, 906, 913, 428/220, 409, 212, 343, 354, 355, 516, 506, 500; 156/183, 184, 196, 210

[56] References Cited

U.S. PATENT DOCUMENTS

| | | |
|---|---|---|
| 1,760,820 | 5/1930 | Drew . |
| 2,532,011 | 11/1950 | Dahlquist et al. ................. 154/53.5 |
| 2,553,816 | 5/1951 | Ebel .................................... 117/122 |
| 2,607,711 | 8/1952 | Hendricks .......................... 117/122 |
| 2,889,799 | 6/1959 | Korpman ........................... 116/114 |
| 3,078,182 | 2/1963 | Crone & Pike .................... 117/68.5 |
| 3,258,312 | 6/1966 | Olson ................................... 23/232 |
| 3,318,852 | 5/1967 | Dixon ................................. 260/78.5 |
| 3,396,837 | 8/1968 | Schmelzle et al. ................... 206/59 |
| 3,523,011 | 8/1970 | Bhiwandker et al. ................ 23/253 |
| 4,137,362 | 1/1979 | Miki et al. .......................... 428/910 |
| 4,139,669 | 2/1979 | Chang ................................ 428/167 |
| 4,188,437 | 2/1980 | Rohowetz .......................... 428/199 |
| 4,237,889 | 12/1980 | Gobran .............................. 128/287 |
| 4,769,283 | 9/1988 | Sipinen et al. ....................... 428/40 |
| 4,781,957 | 11/1988 | Brown et al. ........................ 428/43 |

Primary Examiner—Ellis P. Robinson
Assistant Examiner—P. J. Ryan
Attorney, Agent, or Firm—Donald M. Sell; Walter N. Kirn; Jennie G. Boeder

[57] ABSTRACT

Film-backed pressure-sensitive adhesive tape that resembles conventional creped paper-backed masking tape but can be torn cleanly with the fingers, is prepared by extruding an isotactic polypropylene film, passing it through the nip between a rubber roll and a water-cooled embossed steel roll at a temperature and rate such that predominantly crystalline film is obtained. The embossed roll imparts a ridge-and-valley configuration to one surface of the film, valleys extending crosswise of the tape and having a depth greater than half the total film thickness. When the smooth face of the film is coated with pressure-sensitive adhesive, the resultant tape can be torn readily, using only the fingers, in a straight line crosswise of the tape. When subjected to a stretching force in the machine direction (at right angles to the ridges and valleys), the tape elongates uniformly without "necking down." A specific embodiment of this invention is a sterilization indicator tape made with the above described film.

26 Claims, 2 Drawing Sheets

EASY TEAR STERILIZATION INDICATOR TAPE

BACKGROUND OF THE INVENTION

This invention relates to normally tacky and pressure-sensitive adhesive tape, and especially to tape suitable for use as a general purpose masking tape. The invention also relates to a method of making such a tape.

This invention also relates to tape containing a sterilization indicator ink.

The use of pressure-sensitive adhesive tape to mask areas where it is desired not to apply lacquer, paint, etc. dates back well over half a century; cf., e.g., U.S. Pat. No. 1,760,820. This patent discloses the use of creped paper as the backing for the tape, enabling it to be stretched and shaped to conform to curved lines. Many improvements have subsequently been made in the original creped paper masking tape products, including calendering the creped paper in order to reduce its abrasive properties, saturating the paper with rubbery materials, etc. Creped paper masking tape can be severed with a knife, scissors, or a dispenser; it can even be torn by hand, although it is almost impossible to achieve a straight line tear, a fact that sometimes inconveniences and annoys users of the product.

U.S. Pat. No. 3,396,837 discusses conventional creped paper-backed masking tape, disclosing a replacement that is based on a particular kind of pigmented isotactic polypropylene resin film. This film-backed masking tape is said to have a much greater stretch value than typical creped paper masking tape, thereby permitting it to be conformed along severely curved lines while providing a sharp line of demarcation between the masked and unmasked areas. Tape made in accordance with this patent has been commercially available for many years, and, although it provides an inexpensive replacement for creped paper masking tape and is useful in a number of applications, it suffers from certain disadvantages. For example, it is difficult to initiate tear using only one's fingers, the Elmendorf tear test (ASTM Test D689-79) showing a value of 80-100 grams per ply. (By way of reference, the Elmendorf tear values for saturated creped paper masking tape are in the range of 45-75 g/ply.) Additionally, like conventional masking tape products, it is almost impossible to tear in a straight line. A third disadvantage is that, when subjected to a tensile force, the tape does not elongate evenly but instead stretches at what is apparently its weakest portion, resulting in a "necking down," or narrowing and thinning, of one portion of the backing while the remainder retains its original dimensions.

U.S. Pat. No 4,139,669 discloses a "non-knifing plastic adhesive tape" which is said to be "hand tearable" by virtue of "striations," or grooves, that extend across the width of the tape. Depth, width, and pitch of the striations is dependent on the thickness and type of material of the film base used. The 14 working examples utilize polyvinyl chloride plasticized with dioctyl phthalate, an overall thickness of 0.105-0.275 mm, the depth of striation ranging from 0.01 to 0.09 mm and constituting 6.1 to 47.6% of the total thickness. Although the tabulated examples are somewhat hard to read, it appears that the transverse tear strength of the striated films ranges from 35 to 350 grams per ply. This product is not suggested for use as masking tape and is not understood to be commercially available.

A somewhat related product is shown in U.S. Pat. No. 4,237,889, which describes embossing untensilized crystalline isotactic polypropylene or linear high density polyethylene film with a pattern of alternating ridges and valleys on one side, one possible conformation having the valleys extending laterally across the tape at right angles to the sides; cf. FIG. 1 of the patent. The specific use disclosed is in the preparation of tape closures for disposable diapers, where the ridges and valleys extend parallel to the long dimension of the closure, the ridges extending across the presumed line of tear and preventing any tendency of the closure to be torn inadvertently. This patent discloses the extrusion, embossing, and quick quenching of polypropylene film to obtain a product that is tough and ductile, unsuitable for a masking tape.

The use of adhesive tapes in the sterilization indicator art is taught by U.S. Pat. No. 2,889,799, which discloses the combination of a pressure-sensitive adhesive tape and a lamina containing a heat-modifiable dye stuff. The backing used in the described tape may be selected from woven fabric, paper and conventional polymeric film materials such as cellophane, cellulose acetate, polyethylene, polyesters, vinyl chloride, etc.

U.S. Pat. No. 3,078,182 discloses improvements in the autoclave tape sterilization indicator art. Various backings are described including crepe paper, cellulose acetate or polymeric base film. U.S. Pat. No. 3,258,312 discloses sterilization indicator tapes where the inks used as indicators are sensitive to ethylene oxide. The backing used on the described tape is a crepe paper or a synthetic plastic film. U.S. Pat. No. 3,523,011 teaches additional steam sterilization indicator materials, as well as an indicator tape containing the material on a flexible base (backing) having a pressure-sensitive adhesive on the opposite side of the base and with a backsize material overlying the indicating material.

SUMMARY OF INVENTION

The present invention provides an inexpensive polymeric film-backed pressure-sensitive adhesive tape that is useful as a general purpose masking tape. In appearance the tape closely resembles conventional creped paper-backed masking tape, but it has a number of performance advantages over such products. The tape of the invention can be easily torn with the fingers along a straight line at right angles the sides of the tape. Surprisingly, it can also be torn in a straight line parallel to the sides of the tape. When subjected to a stretching force, the tape elongates uniformly throughout the area to which the force is applied, maintaining its original width while permitting it to be used to define sharply curved lines of demarcation.

The tape of the invention comprises an elongate strip of normally tacky and pressure-sensitive adhesive tape wound convolutely upon itself about a core to form a roll. As indicated, it has particular utility for use as a finger-tearable masking tape, comprising in combination a predominantly (preferably 55-65%) crystalline isotactic polypropylene film backing having an overall thickness on the order of 75-115 micrometers with one smooth side and one rough side and a layer of normally tacky and pressure-sensitive adhesive. This adhesive is usually firmly adherently bonded to the smooth side of the film. Compared to creped paper backings, which have an irregular surface, significantly less adhesive (perhaps 20-40% less) is required. The rough side has closely spaced randomly disposed valleys extending substantially at right angles to the lateral edges of said tape. These valleys are separated by ridges and have a depth greater than one-half (preferably 60–70%) of the overall thickness of the film backing, so that the tape has the general appearance of a creped paper masking tape but differs in that it is readily finger-tearable in a straight line at right angles to its lateral edges. Additionally, when subjected to a stretching force parallel to its lateral edges, the tape elongates 40–80%, throughout its length, without reducing significantly in width.

In the sterilization tape embodiment of this invention, the tape is comprised of the film and adhesive as described above with the additional component of an indicator means for determination that the tape has been exposed to a sterilization procedure. Examples of indicator means which are readily available in the art are ink formulations which change color upon being subjected to steam sterilization or ethylene oxide (ETO) sterilization.

Examples of ink formulations of the sterilization tape embodiment are disclosed in U.S. Pat. No. 3,258,312 for ethylene oxide sterilization and in U.S. application Ser. No. 160,649 for steam sterilization, both incorporated herein by reference. The indicator inks may be applied as a marking to the tapes by either contact printing, such as gravure, or ink jet printing techniques to either side of the film. In a preferred embodiment, the ink is gravure printed on either the smooth side or on the rough side of the film. The ink may optionally be contained in a separate color changing layer, such as disclosed in U.S. Pat. No. 3,078,182, incorporated herein by reference.

The adhesives used may be selected from any adhesives commonly used in the adhesive tape art. A preferred adhesive would minimize transfer of the adhesive material to the surface to which the tape is applied. An example of such an adhesive is a phenolic cured pressure sensitive rubber adhesive such as disclosed in U.S. Pat. No. 2,553,816, incorporated herein by reference.

Although a low adhesion backsize (LAB) is not generally required, it may be desirable for inclusion particularly in the sterilization indicator tape aspect of this invention. The preferred low adhesion backsize is an acrylate terpolymer as described in U.S. Pat. No. 2,607,711, incorporated herein by reference. Other formulations for low adhesive backsizes are disclosed in U.S. Pat. Nos. 2,532,011 and 3,318,852, both incorporated herein by reference.

It will be understood that the layers of this tape may be rearranged as may be required by physical limitations of selected adhesives, inks and LAB's, or by desired effects in the appearance of the product. For example, the adhesive may be applied to the rough side of the film with the indicator ink applied to the smooth side and the LAB applied over the ink. In another configuration, the ink may be printed on the rough side of the film and the adhesive applied over the ink on the rough side with the LAB applied to the smooth side of the film.

The film may b supplied without adhesive as an intermediate stage in production or, in the case of film including an indicator means, for use as a sterilization indicator without adhesive. This adhesiveless indicator would be placed on the inside of a bundle to be sterilized.

This tape is made by (a) extruding a film consisting essentially of isotactic polypropylene resin, (b) while the extruded film is still molten, passing it into the nip between a smooth-surfaced silicone rubber-covered support roll and a water-cooled metal chill roll that is surfaced with a negative of the valley-ridge pattern sought to be obtained, the chill roll being maintained at a temperature high enough to ensure that the film will cool slowly enough to attain a predominantly crystalline character, (c) applying a layer of normally tacky and pressure-sensitive adhesive to the smooth side of the film, and (d) winding the tape convolutely upon itself about a core to form a roll.

Both the tape and its method of manufacture are similar to the tape and method of manufacture disclosed in U.S. Pat. No. 4,237,889. In accordance with the present invention, however, the depth of the valleys constitutes a higher percentage of the overall backing thickness; additionally, a higher degree of crystallinity is obtained, as is evidenced by the fact that the backing has an impact strength as measured by ASTM Test D3420-84, of 1.8–3, preferably 2–2.5 kg-cm. When this degree of crystallinity is attained, the cross-direction tear strength of the product (as measured by ASTM Test D689-79) is in the range of 30–50 (preferably 35–45) grams/ply, and the tape can be readily torn by hand along one of the valleys. When subjected to a longitudinal tensile force exceeding the yield point of the film backing, the film elongates at almost all of the valleys, the ridges serving to maintain the original width of the tape. In contrast, the commercial tape corresponding to U.S. Pat. No. 3,396,837 has a typical cross direction tear strength of 80–100 grams, which renders it very hard to tear by hand, and its width narrows as much as 50% at some location (presumably the weakest cross-sectional area) along the length being subjected to a stretching force sufficient to cause the tape to elongate permanently. When tape made in accordance with U.S. Pat. No. 4,237,889 is subjected to these same tests, the impact strength is typically about 5–5.5 kg-cm, and tear strength parallel to the valleys is typically about 120–170 grams, substantially exceeding the force that can conveniently be applied in a hand operation.

Although it has not been possible to obtain a commercial sample of tape made in accordance with U.S. Pat. No. 4,139,669, it has been demonstrated that when the depth of the valleys embossed in the film backing in accordance with the present invention falls below 50% of the total film thickness (as is apparently true of all products disclosed in the said patent, the depths shown in the 14 working examples ranging from 6.1 to 47.6%, averaging 28.8%), tear strength parallel to the valleys is so high that the product cannot be conveniently used. The significance of crystallinity is not recognized by the patentees and, in any event, the nature of the plasticized polyvinyl chloride used in all the working examples is such that the product would tend to stretch and inherently be difficult to tear.

BRIEF DESCRIPTION OF THE DRAWING

As an aid to understanding the invention, attention is directed to the accompanying drawing, in which like numbers refer to like parts in the several views and in which.

DETAILED DESCRIPTION

Figure 1:
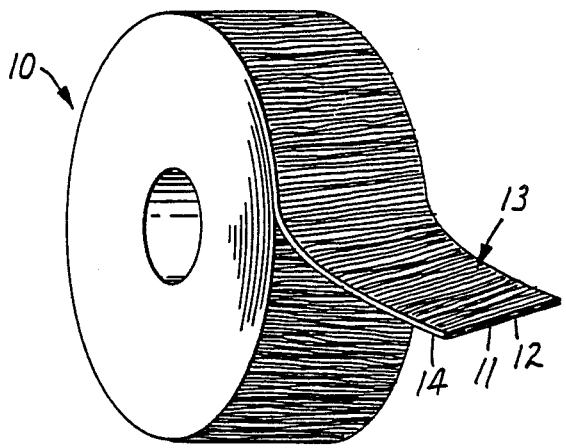
FIG. 1 depicts a roll of tape made in accordance with the invention.

In the drawings FIG. 1 illustrates a convolutely wound roll 10 of normally tacky and pressure-sensitive adhesive tape having crystalline polymeric isotactic polypropylene film backing 11, with smooth face 12 and textured face 13. A layer of normally tacky and pressure-sensitive adhesive 14 is coated over and firmly adherently bonded to smooth face 12.

Figure 2:
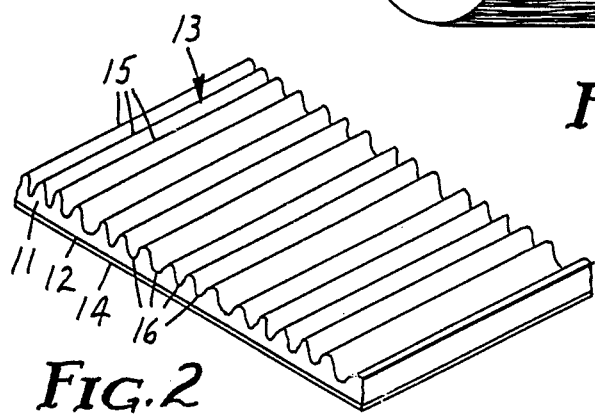
FIG. 2 is an enlarged stylized and somewhat oversimplified perspective view of a portion of the tape shown in FIG. 1, showing the nature of the ridges and valleys in the surface.
Figure 3:
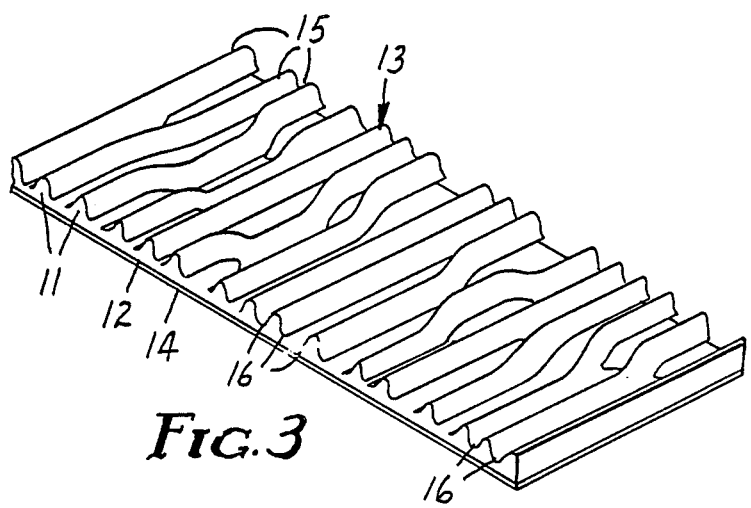
FIG. 3 is similar to FIG. 2, showing the effect of applying a stretching force in a longitudinal direction of the tape sufficient to cause the tape to yield along the area at the bottom of the valleys.

In FIG. 2, which is an enlarged perspective view of a portion of the tape of FIG. 1, textured face 13 is seen to be made up of cord-like ridges 15 separated by valleys 16, the crest of adjacent ridges 15 being about 250–1500 micrometers (especially about 500–1000 micrometers) apart. Not all of the valleys have the same depth, but they average about 50–70% (especially about 65%) of the calipered film thickness. In measuring the caliper of film 11, it is practical to use a conventional thickness gauge of the type in which opposed feet respectively contact smooth face 12 and textured face 13, the foot contacting the latter surface being sufficiently broad to span several ridges 15. The product of the invention closely visually resembles the product of that of U.S. Pat. No. 4,237,889 but differs significantly in its physical properties. The product of U.S. Pat. No. 4,237,889 employs a backing described as a "substantially untensilized, tough, ductile foil of isotactic polypropylene or linear high density polyethylene," the physical properties resulting "from the quick quenching" (cf. Col. 2, lines 37–47), thereby obtaining a film that is not predominantly crystalline. In contrast, the product of the present invention is predominantly crystalline, a characteristic resulting from a comparatively slow quenching of the film during its formation.

Figure 4:
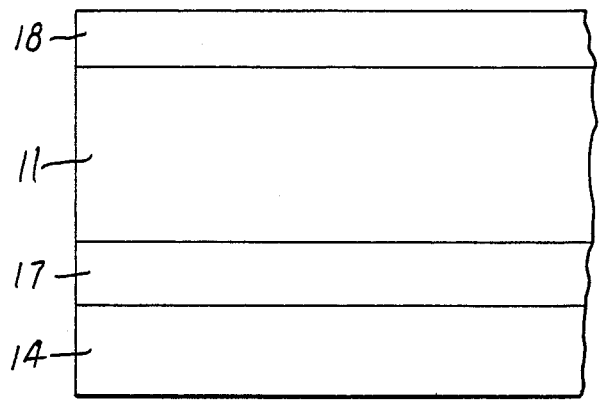
FIG. 4 is a simplified depiction of the relative position of elements of an embodiment of sterilization indicator tape.
Figure 5:
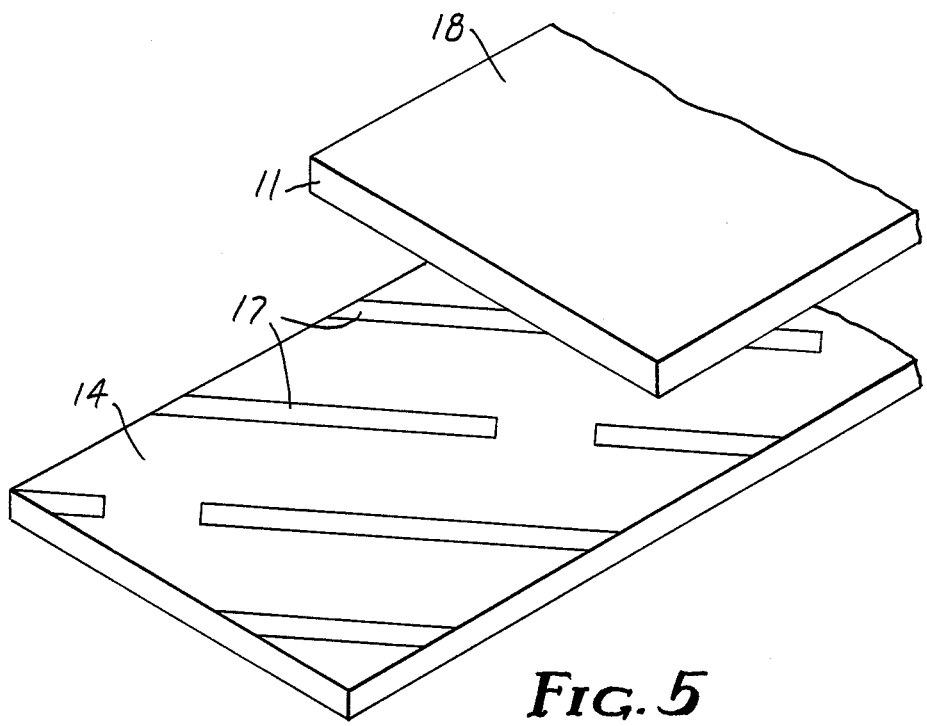
FIG. 5 is an expanded view of an embodiment of the sterilization tape showing diagonal markings of indicator ink between the adhesive and the film backing.

In FIG. 4 and FIG. 5, the additional elements of sterilization indicator ink 17 and low adhesion backsize 18 are shown in their relative positioning with respect to the film 11 and the adhesive 14 in two embodiments of this invention.

Understanding of the invention will be enhanced by referring to the following illustrative but nonlimiting examples, in which all parts and percentages are by weight unless otherwise noted:

EXAMPLE 1

An extrusion composition was prepared by mixing together two parts of a tan pigment concentrate (55% isotactic polypropylene having a melt index of 20 and 45% blend of rutile $TiO_2$, MgO, ZnO, iron oxide and carbon black) and 100 parts isotactic polypropylene ("Dypro" 8771, having a density of 0.905, available from Cosden Oil and Chemical Company). A film was then prepared by extruding the molten polymer blend through a slot extrusion die at a temperature of about 230°–245° C. and then into the nip between a silicone rubber-covered roll and a water-cooled metal chill roll having an engraved random pattern of ridges and valleys extending in the transverse direction, about 20 valleys/centimeter, with an average depth of about 75–90 micrometers, the overall thickness of the extruded film being about 115 micrometers. The temperature of the chill roll was about 40° C., and the film was in contact with the roll for 0.32 second. The resultant film product thus had one smooth surface and one "rough" surface having an appearance similar to that of conventional creped paper masking tape. The smooth surface of the film was then primed using conventional corona discharge techniques to render it more receptive to subsequently applied pressure-sensitive adhesive coatings.

Strips of the film 2.54 cm×25 cm were then prepared, the longer dimension extending in the machine direction (i.e., at right angles to the direction of the ridges and valleys), and allowed to age at 21° C. for at least 7 days to permit the physical properties to reach equilibrium. Each sample was then clamped between the upper and lower jaws of an "Instron" Tensile Tester and the jaws separated at a strain rate of 100%/minute. Elongation at break was found to be 40–80% at an ultimate tensile strength of about 1.8 kg/cm width. It was noted that, even at break, the original 2.54-cm width of the tape was maintained. Several 6.3 cm×7.5 cm samples of film were similarly conditioned and the tear strength parallel to the direction of the ridges and grooves measured in accordance with an Elmendorf-type tear strength tester (cf. ASTM Test D689-79) The average tear strength of the transverse direction was found to be 42 grams per ply, and the film was readily finger-tearable.

The smooth side of the film was then provided with a hot melt coating of a conventional rubber-resin pressure-sensitive adhesive at a coating weight of approximately 21 $g/m^2$. The resultant product was slit to convenient widths and wound convolutely upon itself about a core to form rolls. This tape proved to be useful as a general purpose masking tape. It could be conveniently torn transversely along a straight line, using only the fingers. The tape could similarly be used to conform to sharply curving lines of demarcation without "necking down."

EXAMPLE 2 (Comparative)

Example 1 was repeated, the sole difference being that the average valley depth was about 25–40 micrometers, constituting about 20–35% of the total film thickness. The total elongation at break, at right angles to the ridges and valleys, greater than 300% at an ultimate tensile strength of about 2.6 kg/cm width. During elongation the film, narrowed significantly, reducing its original width by about 25%. The transverse Elmendorf tear strength was found to be about 60–80 grams per ply, making it extremely difficult to tear the film by hand.

When comparative Example 2 is repeated using a smooth surfaced steel chill roll, the results are comparable except that it is essentially impossible to tear the tape transversely along a straight line.

Film backings of the invention have a significantly higher crystallinity than products of the prior art. Using a density column, the product of Example 1 was found to be approximately 60% crystalline. It appears that the crystallinity should fall within the 55–65% range, since more crystalline materials tend to become excessively brittle and fracture rather than tear, while films having significantly lower crystallinity display an excessively high resistance to being torn. The use of a density column to measure crystallinity is complicated when the film being tested contains a filler. Accordingly, it has been found practical and convenient to utilize ASTM Test D3420-84, which provides a standard test method for measuring the pendulum impact resistance of plastic film; the values obtained on this test are inversely related to crystallinity. It has been found that satisfactory ease of finger tear is obtained when the average impact resistance value (using 4 layers of film) is 1.8-3 (preferably 2-2.5) kg-cm. By way of contrast, products made in accordance with U.S. Pat. No. 4,237,889 have an average pendulum impact resistance value on the order of 5-5.5. The impact resistance and crystallinity are directly related to the temperature of the chill roll and time that the extruded film is in contact therewith. To obtain the desired degree of impact resistance or crystallinity, it is necessary to control each of these variables; for example, the chill roll temperature may be lowered if the time the film is in contact with it is decreased.

It will be appreciated that numerous changes can be made by those skilled in the art without departing from the spirit of the invention. For example, the amount and type of filler can be varied, or even eliminated altogether. Similarly, although a low adhesion backsize is ordinarily not required (because of the rough surface), one could be applied in order to increase ease of unwinding a roll of the tape. If desired, minor amounts of other polymers may be blended with the polypropylene. Along the same line minor amounts of other monomers might be copolymerized with propylene.

The sterilization indicator tape aspect of this invention is illustrated by the following nonlimiting examples:

EXAMPLE 3

An extrusion composition is prepared by mixing together 6.5% of a green resin blend (made by blending 2 parts polyethylene/titanium dioxide available from Charles B. Edwards & Co. Inc., Minneapolis, Minn. 55428 with 1 part CBE Green Pigment Concentrate available from Charles B. Edwards & Co. Inc., Minneapolis, Minn. 55428) and 93.5% isotactic polypropylene (Dypro' 8771, having a density of 0.905, available from Cosden Oil and Chemical Company, Big Spring, Tex. 97920) or polypropylene available from ARCO Chemical Co., Philadelphia, Pa. 19101. A film is then prepared by extruding the molten polymer blend through a slot extrusion die at a temperature of about 230°-245° C. and then into the nip between a silicone rubber-covered roll and water-cooled metal embossing chill roll engraved with a random pattern of ridges and valleys extending in the transverse direction, about 20 valleys/centimeter, with an average depth of about 70-90 micrometers, the overall thickness of the extruded film being about 110 micrometers. The temperature of the embossing roll is about 50° C., and the film is in contact with the roll for 0.32 second. The resultant film product thus has one smooth surface and one "rough" surface having an appearance similar to that of conventional creped paper sterilizing tape. The smooth surface of the film is then primed using conventional corona discharge techniques to render it more receptive to subsequently applied indicator ink and low adhesive backsize coatings.

The corona treated film is gravure coated with an indicator ink and a low adhesion backsize on the smooth surface. The ink used is prepared in accordance with the teaching of U.S. Pat. No. 3,258,312 for ethylene oxide sterilization, using the following formulation:

|  | Weight % |
| --- | --- |
| Dye (1,8-dihydroxyanthraquinone) | 1.8 |
| Magnesium Bromide | 43.54 |
| Citric Acid | 8.0 |
| Binder (nitrocellulose base) | 46.66 |

The class of preferred low adhesion backsize is an acrylate terpolymer as described in U.S. Pat. No. 2,607,711.

The "rough" surface is coated with a pressure sensitive adhesive. The adhesive weight is 25-30 gm/m$^2$. The resulting indicator tape jumbo is slit into 2.51 cm × 55.4 linear meter rolls.

EXAMPLE 4

An extrusion composition is prepared by mixing together two parts of a tan pigment concentrate (55% isotactic polypropylene having a melt index of 20 and 45% blend of rutile TiO$_2$, MgO, ZnO, iron oxide and carbon black) and 100 parts isotactic polypropylene ("Dypro" 8771, having a density of 0.905, available from Cosden Oil and Chemical Company, Big Springs, Tex.). A film is then prepared by extruding the molten polymer blend through a slot extrusion die at a temperature of about 230°-245° C. and then into the nip between a silicone rubber-covered roll and water-cooled metal embossing chill roll engraved with a random pattern of ridges and valleys extending in the transverse direction, about 20 valleys/centimeter, with an average depth of about 70-90 micrometers, the overall thickness of the extruded film being about 115 micrometers. The temperature of the embossing roll is about 40° C., and the film is in contact with the roll for 0.32 second. The resultant film product thus has one smooth surface and one "rough" surface having an appearance similar to that of conventional creped paper sterilizing tape. The smooth surface of the film is then primed using conventional corona discharge techniques to render it more receptive to subsequently applied low adhesive backsize coatings.

The corona treated film is gravure coated with an indicator ink on the rough side and a low adhesion backsize on the smooth surface. The ink used is prepared in accordance with the teaching in U.S. application Ser. No. 160,649 for steam sterilization, using the following formulation:

|  |  | Weight % |
| --- | --- | --- |
| Lead Thiosulfate |  | 30.1 |
| Magnesium Carbonate |  | .6 |
| Neocryl B814[1] |  | 20.1 |
| Ethanol |  | 30.1 |
| Ethyl Acetate |  | 22.7 |
| Ink solids | 49% |  |
| Viscosity | 100 cps. |  |

The class of preferred low adhesion backsize is an acrylate terpolymer as described in U.S. Pat. No. 2,607,711.

The "rough" surface is coated with a pressure sensitive adhesive. The adhesive weight is 25-30 gm/m$^2$. The resulting indicator tape jumbo is slit into 2.51 cm × 55.4 linear meter rolls.

EXAMPLE 5

This example shows the pendulum impact resistance of various tape backings using the ASTM Test D3420-84. This test is an indication of ease of finger tear (see Example 2, above).

TABLE 1

| Film Backing | Impact Resistance (kg/cm) | Thickness of Layer (cm) |
|---|---|---|
| Polypropylene Backing of Example 1 | 3 | .010 |
| Polypropylene backing of Example 3 | 2.3 | .0075 |
| Cast polypropylene (Matt finish)[1] | 6 | .0075 |
| Biaxially Oriented Polypropylene[2] | 21 | .0025 |
| Aluminum Foil[3] | 12 | .0006 |
| Polyethylene terephthalate[4] | >50 | .0025 |
| Cellulose acetate[5] | 27 | .0050 |
| Nylon[6] | >50 | .0050 |
| Standard 1224 Tape Backing[7] | 10.5 | .0075 |
| Cloth (acetate)[8] | >50 | N/A |

[1] Commercially available as FDL 285 from 3M, St. Paul, MN
[2] Commercially available as Box Sealing Tape 371 from 3M, St. Paul, MN
[3] Commercially available as High Temperature Flue Tape from 3M, St. Paul, MN
[4] Commercially available as "Mylar" from DuPont de Nemours, E. I. & Co., Inc. Wilmington, DE
[5] Commercially available as "Scotch" Brand Nylon Tape from 3M, St. Paul, MN
[6] Commercially available as "Scotch" Brand Nylon Tape from 3M, St. Paul, MN
[7] Commercially available as Standard 1224 Tape from 3M. St. Paul, MN
[8] Commercially available as "Durapore" Brand Surgical Tape from 3M, St. Paul, MN

We claim:

1. An elongate strip of normally tacky and pressure-sensitive adhesive tape wound convolutely upon itself about a core to form a roll, said tape having particular utility for use as a finger-tearable sterilization indicator tape, comprising in combination a predominantly crystalline isotactic polypropylene film backing having an overall thickness on the order of 75–115 micrometers with one smooth side and one rough side, a layer of normally tacky and pressure-sensitive adhesive, and an indicator means for determination that said tape has been exposed to a sterilization procedure, said rough side having closely spaced randomly disposed valleys extended substantially at right angles to the lateral edges of said tape, said valleys separated by ridges and having a depth greater than one-half the overall thickness, so that the tape has the general appearance of creped paper sterilization indicator tape but differs in that it is consistently readily finger-tearable in a straight line at right angles to its lateral edges, said tape, when subjected to a stretching force parallel to its length, differing from sterilization indicator tape having a smooth-surfaced polypropylene film backing in that it elongates throughout its length without reducing significantly in width.

2. The tape of claim 1 wherein the indicator means is applied as a marking.

3. The tape of claim 2 wherein the indicator means is applied as a marking by gravure printing.

4. The tape of claim 1 wherein the adhesive is located on the smooth side of the film.

5. The tape of claim 4 wherein the indicator means is located between the film and the adhesive.

6. The tape of claim 5 wherein the indicator means is an ink which changes color upon being subjected to steam sterilization.

7. The tape of claim 5 wherein the indicator means is an ink which changes color upon being subjected to ethylene oxide sterilization.

8. The tape of claim 4 wherein the indicator means is located on the rough side of the film.

9. The tape of claim 8 wherein the indicator means is an ink which changes color upon being subjected to steam sterilization.

10. The tape of claim 8 wherein the indicator means is an ink which changes color upon being subjected to ethylene oxide sterilization.

11. The tape of claim 1 wherein the adhesive is located on the rough side of the film.

12. The tape of claim 11 wherein the indicator means is located between the film and the adhesive.

13. The tape of claim 12 wherein the indicator means is an ink which changes color upon being subjected to steam sterilization.

14. The tape of claim 12 wherein the indicator means is an ink which changes color upon being subjected to ethylene oxide sterilization.

15. The tape of claim 11 wherein the indicator means is located on the smooth side of the film.

16. The tape of claim 15 wherein the indicator means is an ink which changes color upon being subjected to steam sterilization.

17. The tape of claim 15 wherein the indicator means is an ink which changes color upon being subjected to ethylene oxide sterilization.

18. The tape of claim 1 wherein the adhesive is a phenolic cured pressure sensitive rubber adhesive.

19. The tape of claim 1 which additionally comprises a low adhesion backsize.

20. The tape of claim 19 wherein the low adhesion backsize is an acrylate terpolymer.

21. A method of making the tape of claim 1 comprising the steps of:
   (a) extruding a film consisting essentially of isotactic polypropylene resin;
   (b) while the extruded film is still molten, passing it into the nip between a smooth-surfaced silicone rubber-covered support roll and a water-cooled metal chill roll that is surfaced with a negative of the valley-ridge pattern sought to be obtained, said chill roll being maintained at a sufficiently high temperature and said film being in contact with said chill roll for a time to ensure that the film will attain a predominantly crystalline character, thereby obtaining a crystalline film having one smooth surface and one rough surface;
   (c) marking a surface of the film with an ink sensitive to either ethylene oxide or to steam sterilization;
   (d) applying a layer of normally tacky and pressure-sensitive adhesive to the smooth side of the film; and
   (e) winding the tape convolutely upon itself about a core to form a roll.

22. Sheet material suitable as a backing for the readily finger-tearable tape of claim 1, said sheet material comprising an approximately 55–65% crystalline isotactic polypropylene film having a 4-ply impact strength of about 1.8–3 kg-cm and an overall thickness on the order of 75–115 micrometers, with one smooth side and one rough side, said rough side having closely spaced randomly disposed valleys extending substantially at right angles to the lateral edges of said sheet material, said valleys being separated by ridges and having a depth of greater than 50% to about 70% of the overall thickness, so that the sheet material has the general appearance of the creped paper backing commonly used in masking tape but differs in that it has an Elmendorf tear strength of about 30–50 grams and is consistently readily finger-tearable in a straight line along one of the valleys, said sheet material, when subjected to a stretching force at right angles to said valleys, elongating throughout its length without reducing significantly in width.

23. The sheet material of claim 22 having an indicator means for determination that said tape has been exposed to a sterilization procedure.

24. The sheet material of claim 23 wherein the indicator means is an ink which changes color upon being subjected to steam sterilization.

25. The sheet material of claim 23 wherein the indicator means is an ink which changes color upon being subjected to ethylene oxide sterilization.

26. A method of making the tape of claim 1 comprising the steps of:
   (a) extruding a film consisting essentially of isotactic polypropylene resin;
   (b) while the extruded film is still molten, passing it into the nip between a smooth-surfaced silicone rubber-covered support roll and a water-cooled metal chill roll that is surfaced with a negative of the valley-ridge pattern sought to be obtained, said chill rolls being maintained at a sufficiently high temperature and said film being in contact with said chill roll for a time to ensure that the film will attain a predominantly crystalline character, thereby obtaining a crystalline film having one smooth surface and one rough surface;
   (c) marking a surface of the film with an ink sensitive to either ethylene oxide or to steam sterilization;
   (d) applying a layer of normally tacky and pressure-sensitive adhesive to the rough side of the film; and
   (e) winding the tape convolutely upon itself about a core to form a roll.

* * * * *

UNITED STATES PATENT AND TRADEMARK OFFICE
CERTIFICATE OF CORRECTION

PATENT NO. : 4,898,762
DATED : February 6, 1990
INVENTOR(S) : Josephine S. Brown and Alan J. Sipinen It is certified that error appears in the above-identified patent and that said Letters Patent is hereby corrected as shown below:

Col. 8, Line 61, insert -- [1] Commercially available from Polyvinyl Chemie, Waalwiuk, Netherlands --

Signed and Sealed this

Thirteenth Day of August, 1991

Attest:

HARRY F. MANBECK, JR.

Attesting Officer

Commissioner of Patents and Trademarks